United States Patent

Koni et al.

[11] 4,345,612
[45] Aug. 24, 1982

[54] ANESTHETIC GAS CONTROL APPARATUS

[75] Inventors: Tuyoshi Koni; Yoshihisa Urushida; Akira Tsuzuki, all of Tokorozawa, Japan

[73] Assignee: Citizen Watch Company Limited, Tokyo, Japan

[21] Appl. No.: 157,581

[22] Filed: Jun. 9, 1980

[30] Foreign Application Priority Data

Jun. 12, 1979 [JP] Japan .................................. 54-73835

[51] Int. Cl.³ ............................................ G05D 11/13
[52] U.S. Cl. ................................ 137/101.19; 137/554; 128/203.14; 128/203.25; 128/204.21
[58] Field of Search ........................ 137/101.19, 101.21, 137/DIG.1, 554, 599; 73/718, 861.52; 128/203.12, 200.19, 204.21, 203.14, 203.25; 340/711, 712, 627, 629, 636, 663, 522

[56] References Cited

U.S. PATENT DOCUMENTS

| | | | |
|---|---|---|---|
| 3,025,868 | 3/1962 | Jaquith et al. | 137/DIG. 1 |
| 3,036,585 | 5/1962 | Shawhan | 137/101.19 |
| 3,056,417 | 10/1962 | Greaves | 137/DIG. 1 |
| 3,219,046 | 11/1965 | Waugh | 137/101.19 |
| 3,272,217 | 9/1966 | Young | 137/101.19 |
| 3,318,153 | 5/1967 | Lode | 73/718 |
| 3,351,057 | 11/1967 | Goodyear et al. | 128/203.12 |
| 3,895,367 | 7/1975 | Visser | 340/629 |
| 4,001,807 | 1/1977 | Dallimonti | 340/711 |
| 4,215,409 | 7/1980 | Strowe | 128/203.14 |
| 4,224,615 | 9/1980 | Penz | 340/712 |
| 4,228,815 | 10/1980 | Juffa et al. | 137/98 |
| 4,242,676 | 12/1980 | Piguet et al. | 340/712 |

*Primary Examiner*—H. Jay Spiegel
*Attorney, Agent, or Firm*—Jordan and Hamburg

[57] ABSTRACT

An apparatus for supplying a mixture of oxygen and an anesthetic gas at a predetermined flow rate and mixture ratio. The flow rate and mixture ratio are controlled by means of electrically operated throttle valves, responsive to output signals from an electronic control system, generated in accordance with data stored in the control system and with input signals applied to the computer from means for sensing the flow rates of the oxygen and anesthetic gas. Desired flow rate and mixture ratio data may be input by using a numeric keyboard, and are digitally displayed.

8 Claims, 13 Drawing Figures

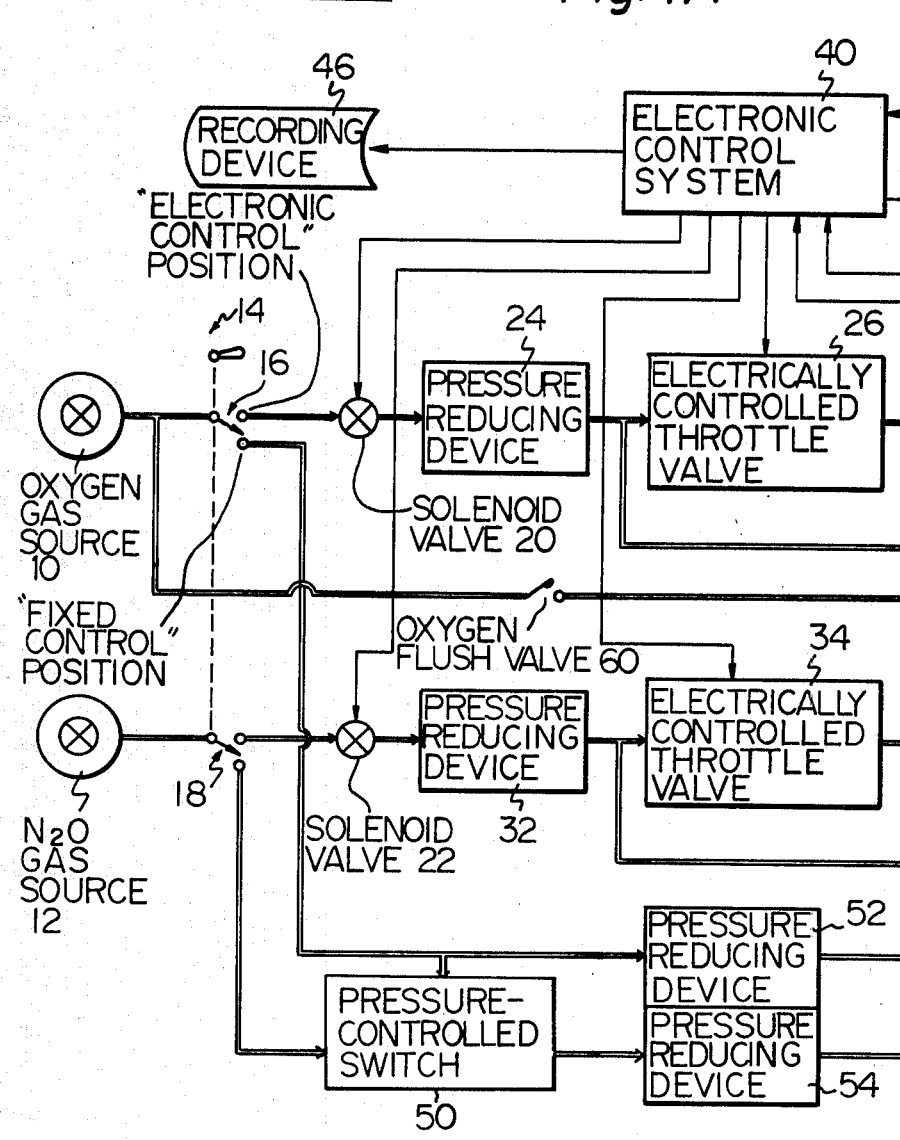

| Fig. 6A | Fig. 6B |

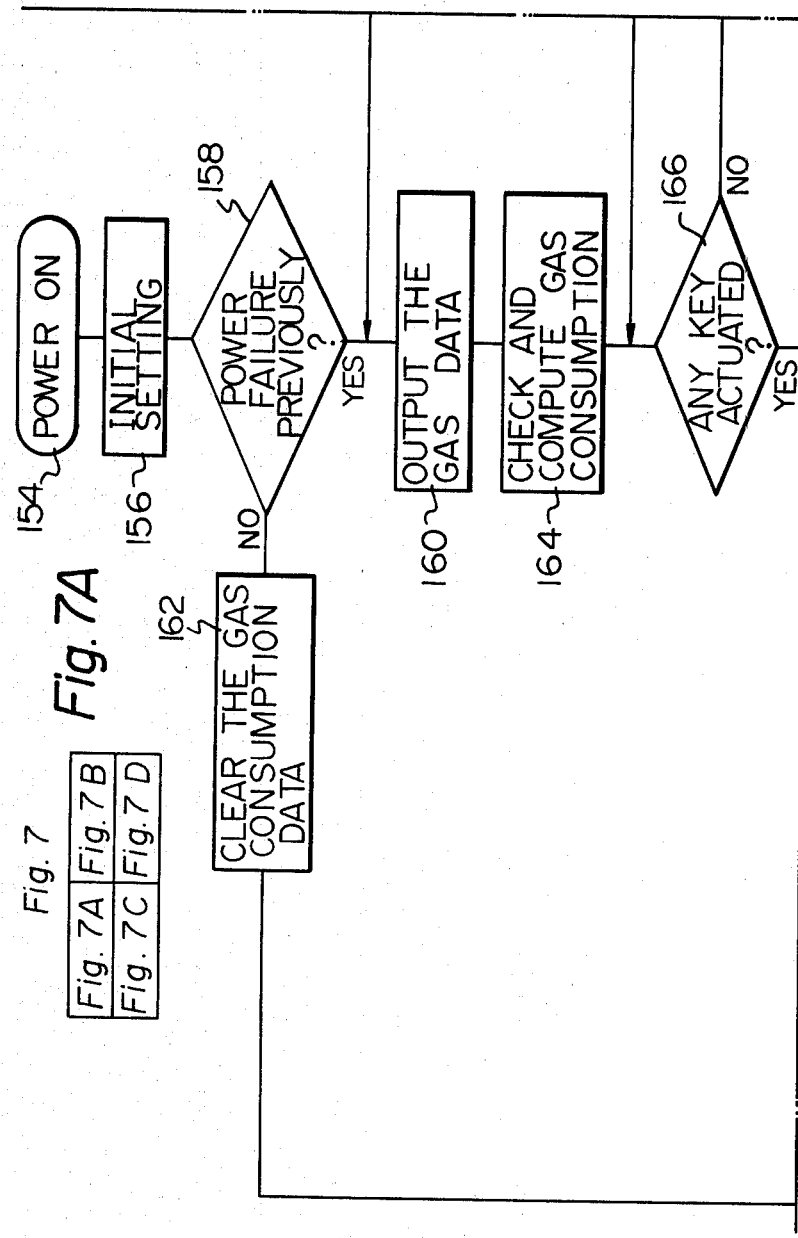

ANESTHETIC GAS CONTROL APPARATUS

BACKGROUND OF THE INVENTION

This invention relates to an apparatus for providing a controlled supply of an anesthetic gas.

In recent years, various improvements have been made in surgical equipment, in line with advances in medicine generally. However, in the case of the supply of an anesthetic gas, manual control is still the normal method adopted. This presents various disadvantages, including the possibility of operator error and the difficulty of maintaining an accurately controlled supply of the anesthetic gas. At present there is on the market a system for the supply of anesthetic gas which is designed to overcome the effects of operator error by accurately regulating the flow rate of the gas and the mixture ratio in an interlocking manner. However this system, as well as the conventional manual method has the disadvantage that accurate measurement and recording of the progress of the anesthetic process are difficult to accomplish. In addition, these systems utilize a type of gas flow rate meter which becomes inaccurate when the apparatus is tilted.

With the present invention, such disadvantages of the prior art methods are overcome effectively. Flow rates of gases used to constitute the anesthetic gas mixture are monitored by flow rate sensors which produce electrical signals in response. These are applied to an electronic computer, output signals from which regulate the flow of gases by means of actuating electrically controlled throttle valves. In this way, the flow rate and mixture ratio of anesthetic gas are accurately determined in accordance with data stored beforehand in a memory of the electronic computer.

SUMMARY OF THE INVENTION

The present invention comprises an apparatus for providing a precisely regulated flow of an anesthetic gas comprising a mixture of $O_2$ and a gas such as $N_2O$, with the flow rate and mixture ratio of the anesthetic gas being accurately determined in accordance with data stored in an electronic control system. Signals indicating the flow rate of the $O_2$ and the other gas (e.g. $N_2O$) are generated by means of flow rate sensors, and are input to the electronic control system. Output signals from the control system, whose values are computed from the flow rate input data and the stored data, are applied to electrically controlled throttle valves to regulate the flow of the gases. After leaving the throttle valves, the gases are combined to form the anesthetic gas mixture. Data which is to be stored in the computer to determine the flow rate and mixture ratio of the anesthetic gas is input by means of a numeric keyboard. Information on flow rate and mixture ratio can be displayed when required during the supply of the anesthetic gas, as can the cummulative gas consumption information, by means of digital display sections. Means are provided whereby, in the event of a power failure, changeover to supply of anesthetic gas at a fixed, predetermined flow rate and mixture ratio can be immediately accomplished. In addition, in the event of power failure, data previously input to determine the desired flow rate and mixture ratio are retained within a nonvolatile memory area, and are made immediately available when power is restored to the equipment.

DESCRIPTION OF THE PREFERRED EMBODIMENT

Figure 1B:
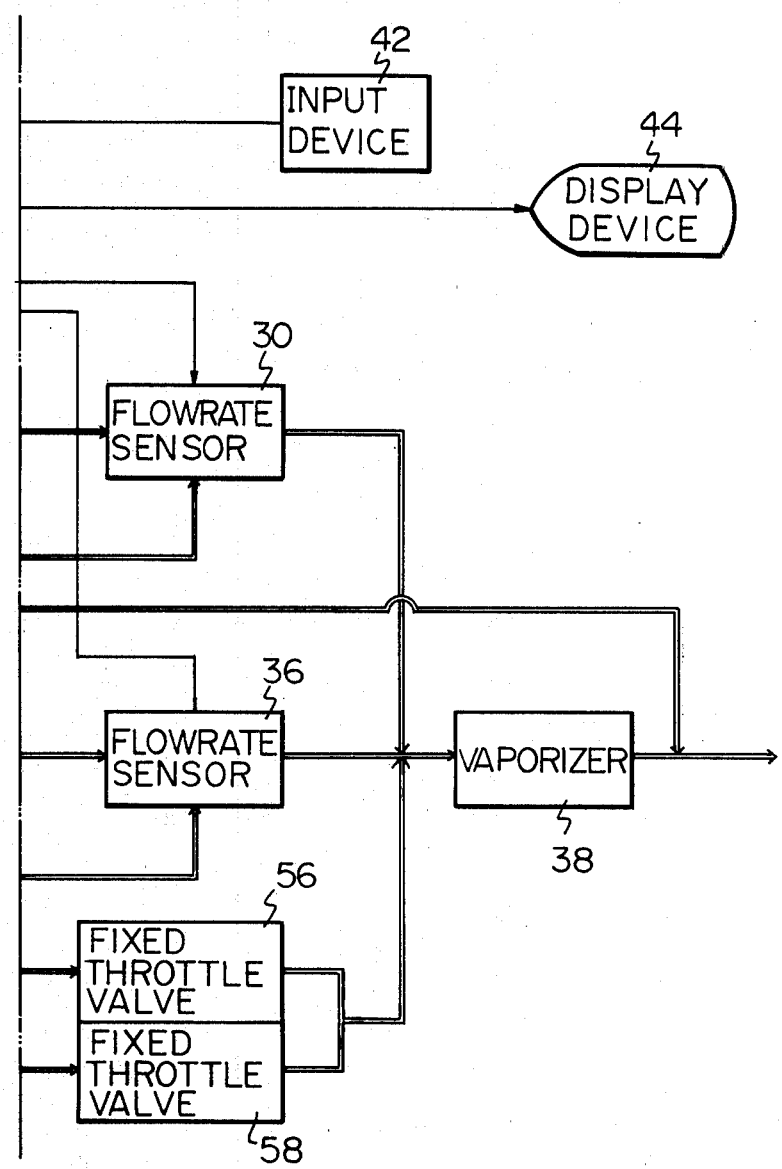
FIG. 1 is a block diagram illustrating the principal features of an anesthetic gas supply apparatus according to the present invention.

Referring first to FIG. 1, a general block diagram is shown therein of an embodiment of an apparatus for the controlled supply of an anesthetic gas according to the present invention. Reference numeral 10 denotes a source of $O_2$ gas, while numeral 12 denotes a source of $N_2O$ gas. Although not indicated in FIG. 1, each of gas sources 10 and 12 may comprise a plurality of gas sources, one or more of which may be used as a reservoir supply. In this case, shuttle valves may be provided to interconnect sources of the same gas. Numeral 16 denotes a $O_2$ changeover valve, and numeral 18 an $N_2O$ changeover valve. These may be simultaneously changed over between a position in which the flows of $O_2$ and $N_2O$ are electronically controlled, as described below, and another position in which predetermined flow rates are fixed for the gases. This switching over is performed manually by actuation of a changeover handle 14. Numerals 20 and 22 denote solenoid valves. These should preferably attain a closed condition when no current is passed through their solenoids, to thereby be automatically closed in the event of power failure. Numerals 24 and 28 denote pressure regulators, which act to reduce the pressure of $O_2$ supplied from solenoid valve 20 and $N_2O$ supplied from solenoid valve 22, respectively. Numerals 26 and 34 denote electrically controlled throttle valves. These are responsive to applied electrical signals, generated as described hereinbelow, for regulating the flows of $O_2$ and $N_2O$ gases supplied from pressure reducing devices 24 and 32 respectively. Throttle valves 26 and 34 may for example be actuated by electromagnetic forces, to thereby vary the size of openings through which the gases are passed. Alternatively, a thermal valve such as that disclosed in U.S. Pat. No. 3,650,505 may be utilized, in which valve opening is controlled by heat expansion of an actuator. Numerals 30 and 36 denote flowrate sensors, which comprise means for measuring the flowrates of the $O_2$ and $N_2O$ gases from throttle valves 26 and 34 respectively. Various types of device are suitable for use as flowrate sensors. For example, the rotational speed of a shaft having vanes attached thereto to be rotated by the gas flow may be measured. Such rotational speed measurement could for example by accomplished electronically by utilizing photo-electric emitting and receiving diodes. Another possible method is to heat the flowing gas, and to measure the amount of thermal change caused by the flow rate. Such a method is disclosed in U.S. Pat. No. 3,938,384. Still another method is to transmit ultrasonic waves through the gas flow, and to measure changes in the received signal caused by the rate of flow of the gas. It is also possible to measure the flowrate by measuring the numbers or sizes of vortices which are developed within the gas flow. The preferred method for the present invention is to measure the pressure differential developed across each of the throttle valves 26 and 34. Two electrodes are mounted adjacent to one another, with one of the electrodes being deformable by the pressure differential developed across a throttle valve. This deformation causes a change in the capacitance between the electrodes, which is measured electronically to thereby determine the gas flowrate. However, although the latter method is preferred, it is equally possible to utilize any of the other methods of determining gas flowrate referred to above, so long as sufficient reproducibility of measurement is assured. Such reproducibility is ensured by the preferred gas flowrate measurement method mentioned above.

The $O_2$ and $N_2O$ gases from the flowrate sensors are mixed and passed through a vaporizer 38 to be mixed with a vapor such as halothane or fluothane, in order to enhance the efficacy of the anesthetic gas. The resultant anesthetic gas is then output from the system to be passed to the patient.

Numeral 40 denotes an electronic control system, which generates signals to control throttle valves 26 and 34, and solenoid valves 20 and 22, and receives signals generated by flowrate sensors 30 and 36. These control signals are determined on the basis of data which is stored in a fixed manner within memory areas in control system 40 (e.g. by means of read-only memory devices, wired memory devices etc) and data which is input to the control system for temporary storage by means of an input device 42. In the preferred embodiment, input device 42 comprises a plurality of key switches. Data which is stored in control system 40 or is being input thereto to be stored is displayed by means of a display device 44. A recording device such as a printer unit may be coupled to control system 40.

As stated above, changeover valves 16 and 18 can be manually set to a position in which fixed, predetermined values for the flow rate and mixture ratio of the anesthetic gas are applied. In this case, $N_2O$ gas is supplied from source 12 to a pressure-controlled switch 50, which only attains an open condition when the pressure of $O_2$ gas from source 10 is above a predetermined minimum level. This is provided as a precautionary measure, so that there is no possibility of an anesthetic gas containing an excessively low proportion of oxygen being supplied in the event that changeover from electronically controlled operation to fixed flowrate and mixing ratio operation is performed when $O_2$ gas source 10 is almost depleted. $O_2$ and $N_2O$ are thereafter passed through pressure reducing devices 52 and 54 respectively, and from these pass through fixed throttle valves 56 and 58 respectively. The outputs from fixed throttle valves 56 and 58 are then combined to form an anesthetic gas having a predetermined flow rate and mixture ratio, which is then passed through vaporizer 38 and is output to the patient.

The term "electronic control system" is used in this specification in referring to the electronic control means of the present invention. It should be understood that this term is meant to include an assemblage of one or more integrated circuits or one or more integrated circuit chips which individually perform microprocessing functions, data storage functions, and so on. Display device 44 may comprise a liquid crystal display, a light emitting diode display, or other suitable means for displaying numeric data.

Reference numeral 60 denotes an oxygen flush valve. This serves to pass a flow of pure oxygen to the output from vaporizer 38 when actuated, and is used, for example, to resuscitate the patient, when necessary.

Figure 2:
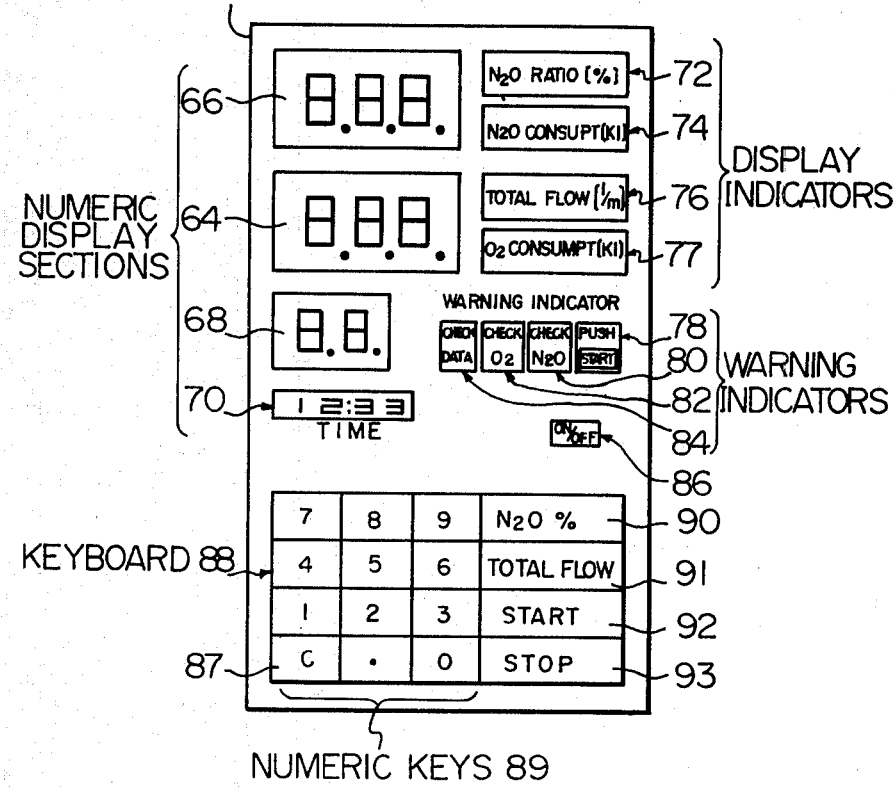
FIG. 2 is a front view of a control panel of an anesthetic gas supply stream according to the present invention, whereby data may be input and previously input data displayed digitally.

Referring now to FIG. 2, a front view of a control panel provided on the control apparatus of the present invention is shown. This is utilized to input data concerning desired gas flowrate and gas mixture ratios, and to display such data as well as cumulative gas consumption data. Numeral 64 denotes a numeric display section which displays either the total flowrate of anesthetic gas from the apparatus (e.g. in liters per minute) or the cumulative consumption of oxygen. Numeral 66 denotes a numeric display section which displays either the mixture ratio of the anesthetic gas (e.g. the relative proportions of $O_2$ and $N_2O$ by volume), calculated on a per minute basis, or the cumulative consumption of $N_2O$ gas. An indicator 72 lights to indicate when display section 67 is displaying the mixture ratio of the anesthetic gas, while an indicator 74 lights to indicate that display section 66 is displaying the cumulative consumption of $N_2O$. An indicator 76 lights to indicate that display section 64 is displaying the total flowrate of the anesthetic gas, while an indicator 77 lights to indicate that display section 64 is displaying the cumulative consumption of $O_2$.

Data specifying the total flowrate of anesthetic gas and the mixture ratio are input by means of numeric keys 89 on a keyboard 88. When such data is input, it is first displayed temporarily on a monitor display section 68. Input of data is controlled by means of a set of keys 90, 91, 92 and 93 as will be described hereinafter.

The control panel 67 further comprises a set of warning indicators. One of these, denoted by numeral 84, goes on to indicate that data has been input which is invalid, i.e. which does not fall within a range of values stored in the control system 40. Warning indicator 78 serves to prompt the operator to initiate operation of the apparatus at certain steps during the input of data, and also, if too long a time elapses between input of data and the start of operation. Warning indicator 80 indicates that the supply of $N_2O$ gas may be deficient, e.g. due to the gas source becoming exhausted, while warning indicator 82 indicates that the supply of $O_2$ may be deficient. Each of the indicators 72 to 84 may include a lamp such as a light emitting diode or incandescent lamp. Numeral 86 denotes a power on/off switch. Numeral 70 denotes a clock display section.

Figure 3:
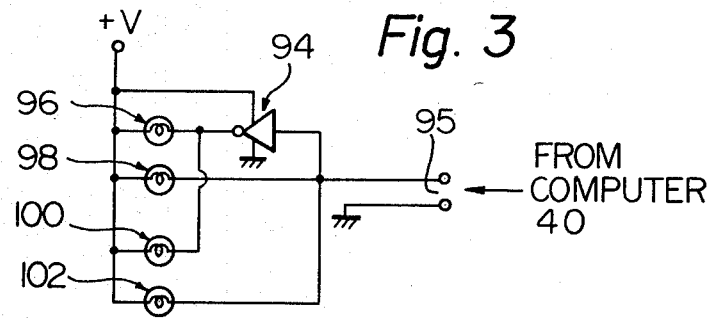
FIG. 3 is a circuit diagram of a circuit for driving indicator lamps in the control panel of FIG. 2.

FIG. 3 is a wiring diagram of a circuit for driving lamps of display indicators 72, 74, 76 and 77. Each of these indicators may consist of a semi-transparent panel, behind which is one of a set of lamps 96, 98, 100 and 102. The circuit further includes an inverter 94, the output of which is coupled to lamps 96 and 100. A signal from the output of computer 40 is coupled to drive lamps 98 and 102, and also to the input of inverter 94. It can be seen that when the input signal, appearing on terminals 95, is at a high level, then lamps 96 and 100 will light, as the output of inverter 94 goes to a low level, while when the input signal on terminals 95 is at a low level, lamps 98 and 102 will light. In this way, a single signal line from computer 40 serves to control the four display indicators 72, 74, 76 and 77 of control panel 67.

Figure 4:
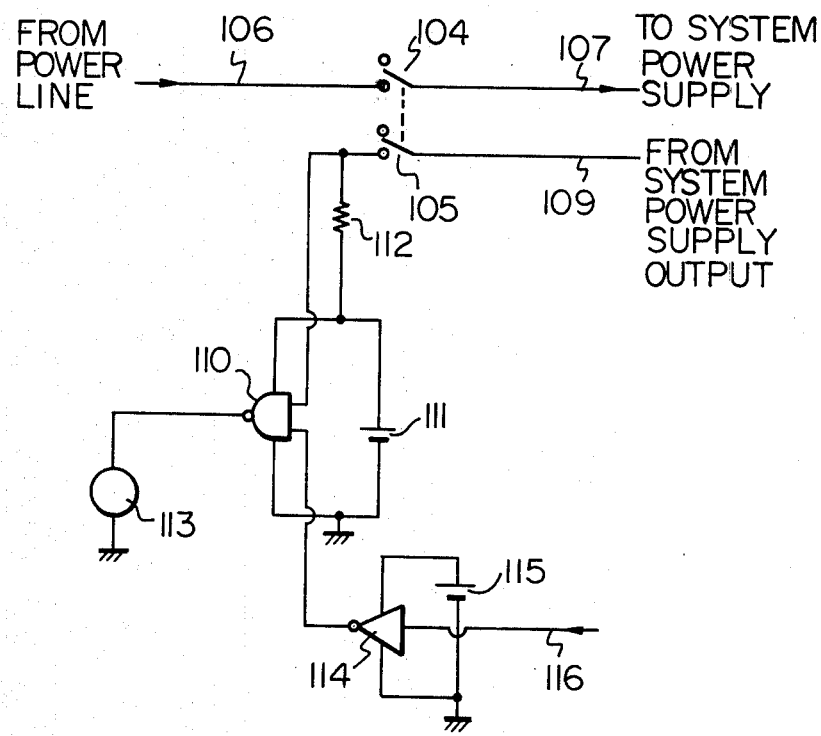
FIG. 4 is a circuit diagram of a circuit whereby an audible alarm warning signal is generated automatically in the event of a power supply failure.

FIG. 4 is a circuit diagram of a circuit whereby a buzzer sounds an audible alarm signal in the event of a power supply failure while the apparatus is in operation, or in the event of some abnormal condition being detected by electronic control system 40. Numerals 104 and 105 denote switches which are coupled together to be actuated simultaneously. Switch 104, when closed, supplies power from a power line 106 to the system power supply section, via a line 107. An output supply voltage produced from the system power supply section is connected to a line 109, so that when switch 104 is closed to apply power to the control system, the supply voltage appearing on line 109 is applied to one input of a NAND gate 110. NAND gate 110 is supplied with power by means of a battery 111, which serves to ensure that NAND gate 110 will remian operative in the event of system power failure. An alarm signal from the control system is applied on a line 116, in the event of an abnormal operating condition being detected by the control system while the system is in use. Line 116 is coupled to the input of an inverter 114, which is also powered by a battery, denoted by numeral 115, so as to be independent of power supply failure. If convenient, both NAND gate 110 and inverter 114 may both be powered from the same battery, of course. The output from inverter 114 is coupled to a second input of NAND gate 110. The output of NAND gate 110 is coupled to a device for generating an audible alarm signal, such as a piezoelectric buzzer, denoted by numeral 113. The high potential side of battery 111 is coupled to the same input of NAND gate 110 as the output from switch 105.

The operation of this circuit is as follows. With power to the system switched off, i.e. with switches 104 and 105 in the closed condition, a high level signal will be applied to one input of NAND gate 110 through resistor 112 from battery 111. In addition, since the potential of line 116 will be zero at this time, the output from inverter 114 will be at the high level. As a result, the output from NAND gate 110 will be at the low level (i.e. zero volts) so that buzzer 113 will be inoperative. If now power is switched on, then a high level signal will appear on line 109 from the system power supply section, so that the output from switch 105 will maintain the corresponding input of NAND gate 110 at the high level. If the control system detects no abnormal operating condition, then the signal appearing on line 116 will be at the low level at this time, so that high level signals are applied to both of the inputs of NAND gate 110, thereby maintaining buzzer 113 in the inoperative condition. If now a power failure should occur (either due to loss of the input power on line 106 or due to a fault within the power supply section of the control system), then the signal appearing on line 109 will go to the low level, so that the output from NAND gate 110 will go to the high level condition. This results in buzzer 113 being activated to sound an audible alarm signal.

If, on the other hand, a power failure does not occur, but control system 40 detects some abnormal operating condition, then control system 40 sets the signal appearing on line 116 to the high level condition. As a result, a low level signal is applied from inverter 114 to NAND gate 110 input, so that the output from NAND gate 110 does to the high level state, thereby activating buzzer 113 to produce an audible alarm signal.

The operation of the preferred embodiment will now be described, referring first to FIG. 1. During normal operation, changeover handle 14 is set in the position in which electronic control is performed, i.e. the position in which $O_2$ and $N_2O$ are supplied from sources 10 and 12 respectively to solenoid valves 20 and 22. Once data has been entered into control system 40 to specify the desired flow rate and mixture ratio of the anesthetic gas, and operation of the apparatus has been activated, solenoid valves 20 and 22 are opened, thereby passing $O_2$ and $N_2O$ gases to the pressure reducing devices 24 and 32, in which the gases are reduced in pressure to a suitable level. The gases then pass to electrically controlled throttle valves 26 and 34.

Electrical signals produced by electronic computer 40 determine the rates of flow through throttle valves 26 and 34. These electrical signals are determined in accordance with data stored in the computer beforehand and data which is produced by flowrate sensors 30 and 36. The stored data, which specifies the desired total flowrate and the mixture ratio, are compared with output data provided by the signals from flowrate sensors 30 and 36, and the signals applied to electrically controlled throttle valves 26 and 34 are modified in such a way as to compensate for any differences between the actual total flow rate and mixture ratio and the stored values for these parameters. If necessary, the progress of this throttling control operation may be recorded by signals applied from computer 40 to recording device 46.

The anesthetic gas having the preset flow rate and mixture ratio is then passed through vaporizer 38, and from there is passed to the patient.

When it is necessary to rapidly supply a large volume of oxygen gas, for example in order to resuscitate a patient, this is accomplished by actuating oxygen flushing valve 60.

In the event of a power failure during a surgical operation, changeover handle 14 is immediately set to the "fixed control" position by the operator. Oxygen is then passed to a pressure reducing device 52 and, if the oxygen pressure is above a predetermined minimum level, $N_2O$ gas is passed through a pressure controlled switch 50 to pressure reducing device 54. This serves to eliminate the possibility that an anesthetic gas containing too low a proportion of oxygen will be supplied to the patient due to the oxygen source 10 being almost depleted. The $O_2$ and $N_2O$ gases are then set to predetermined fixed flowrates by means of fixed throttle valves 56 and 58, and then passed through vaporizer 38 to the patient.

The method of operation of control panel 67 will now be described, with reference to FIG. 2. Data are input by means of numeric keys 89, together with a clear key 87 and control keys 90, 91, 92 and 93. These keys correspond to input device 42 of FIG. 1. In order to input data specifying a desired total flow rate or mixture ratio, numeric keys 89 are actuated. The number thus input is first displayed on monitor display section 68. Various methods of handling the numeric data input by the keyboard, before storage within the computer, are possible. In this embodiment, the monitor display section is only capable of displaying two digits (although this may of course be changed to permit display of a larger number of digits if desired). It is possible, for example, to arrange that if the operator inputs more than two digits in succession from keyboard 88, this will be treated as an error.

Alternatively, it can be arranged that the first digit input appears first in the least significant position of the monitor display section, the next digit input causes the first digit to move to the most significant position of the monitor display section and the second digit to appear in the least significant position, the next digit input from the keyboard appears in the least significant display position while the previously input digits are shifted upwards (so that the first digit input is discarded), and so on. The particular method adopted will be determined by the operating program of electronic control system 40.

Once the input data is displayed on monitor display section 68, then if this data is to designate the mixture ratio of the anesthetic gas, the operator depresses the control key 90, which is marked "N$_2$O%". The input data then appears in display section 66, and display indicator 72 lights up. If the input data is to designate the total flow of anesthetic gas, then the operator depresses the control key 91, marked "TOTAL FLOW". This causes the input data to appear in display section 64, and the display indicator 76 lights up. When the input data is displayed on both display sections 66 and 64, the control system 40 then judges whether the input data is valid, i.e. is within predetermined limit values for the total gas flow and the proportion of N$_2$O gas. For example, a mixture ratio corresponding to a proportion of N$_2$O gas of 100% and a total flow of 0.1 liters per minute would be judged as abnormal. In such a case, the circuit shown in FIG. 4 and described above is activated by the control system to generate an audible alarm signal, and the "CHECK DATA" warning indicator 84 of the control panel is illuminated. The operator then must input corrected data.

The above are a set of preliminary operations, at the end of which the desired flow rate and mixture ratio are displayed on display sections 64 and 66. If the apparatus is not then set into actual operation within a predetermined minimum time period, the warning indicator 78 "PUSH START" on the control panel is illuminated and an audible alarm signal is emitted. This is a precaution in case the operator should assume that the apparatus is in operation after the data has been input. If would be possible to arrange that the apparatus goes into operation immediately after the completion of input of data. However this would not provide the operator with the opportunity to check that the data is correct, and would therefore be hazardous.

In order to set the apparatus into actual operation, the operator must actuate the "START" key 92. Electrical signals produced by control system 40 thereupon cause solenoid valves 20 and 22 to open, and begin to control the throttle valves 26 and 34 to regulate the flows of O$_2$ and N$_2$O so as to provide the desired flow rate and mixture ratio. The control signals applied throttle valves 26 and 34 are determined by the control system in accordance with the previously entered data and the output signals produced from flowrate sensors 30 and 36.

As described above, the circuit shown in FIG. 4 will cause an audible alarm signal to be generated in the event of a power supply failure during operation of the apparatus, due to such reasons as a fault in the power supply circuitry of the apparatus, a loss of power on the input power line, accidental withdrawal of a power line plug from its socket, the blowing of a fuse, and so on. In such a case, no visual indication will be given of the failure, due to the loss of power for driving indicator lamps. In addition, a high level signal will be delivered to the audible alarm circuit, on line 116, in the event of any of a number of possible abnormal operating conditions occurring during operation of the apparatus, causing an audible alarm warning to be generated. For example, if the value of the output signal from flowrate sensor 30 or 36 should vary from the value which is set by the previously input data, and if this discrepancy in the flowrate should persist unaffected by the action of throttle valve 26 or 34, then an alarm signal will be generated. Such a case can occur if the oxygen source 10 or the N$_2$O source 12 becomes exhausted, or if a blockage should occur in one of the gas lines. If the flow of oxygen is found to be insufficient, in such an event, then the warning indicator 82 "CHECK O2" will go on, together with the audible alarm signal. If the flow of N$_2$O is found to be insufficient, then the warning indicator 80 "CHECK N$_2$O" will go on, together with the audible alarm signal.

To terminate operation of the apparatus, the key 93 "STOP" must be depressed. When this is done, control system 40 generates control signals causing solenoid valves 20 and 22 to close, and outputs cumulative gas consumption data to be displayed on control panel 67. The cumulative consumption of N$_2$O is displayed on display section 66, and the cumulative consumption of O$_2$ is displayed on display section 64. At the same time, a signal is applied by control system 40 to the circuit shown in FIG. 3, which causes lamps 98 and 102 to be turned on, thereby illuminating display indicators 74 and 77, to indicate that the cumulative consumptions of O$_2$ and N$_2$O are being displayed.

Figure 5:
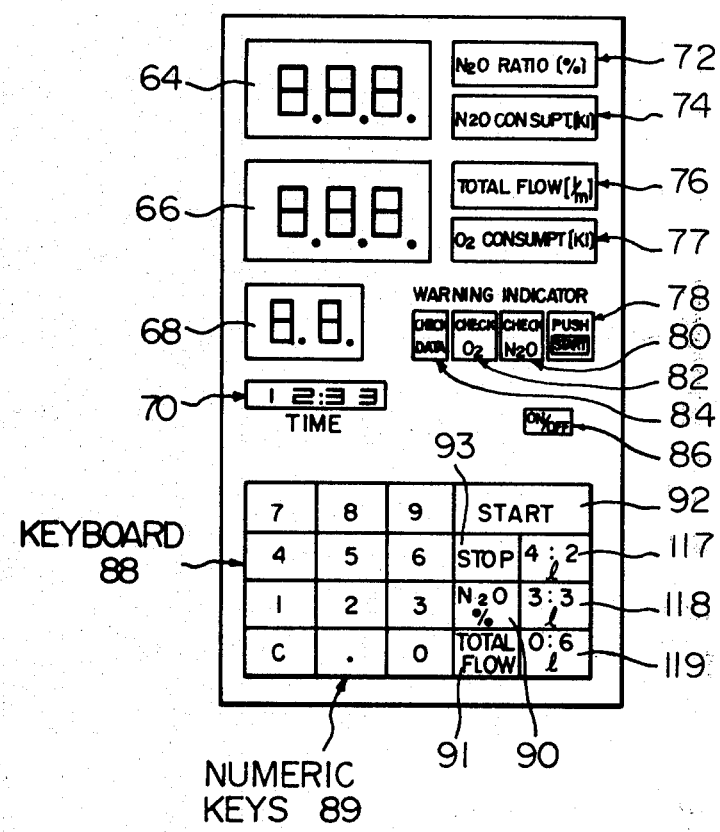
FIG. 5 is a front view of a second embodiment of a control panel for an anesthetic gas supply apparatus according to the present invention.

FIG. 5 shows another embodiment of a control panel for a gas control apparatus according to the present invention, which provides some additional functions. Except for keyboard 88, the control panel of FIG. 5 is functionally and structurally identical to that of FIG. 2. However in the example of FIG. 5, the keyboard 89 is provided with three additional keys, denoted by numerals 117, 118 and 119. These enable predetermined, commonly used flowrates and mixture ratios to be immediately selected. The data specifying these flowrates and mixture ratios are input to the control system 40 beforehand, and stored therein. Actuation of any one of keys 117, 118 or 119 causes a particular predetermined flow rate and mixture ratio to be selected, i.e. three different anesthetic gas conditions. For the example of FIG. 5 these are, firstly, a flowrate of N$_2$O of 4 liters per minute with an oxygen flowrate of 2 liters per minute, i.e. a mixture ratio of approximately 67%, secondly, equal flowrates of O$_2$ and N$_2$O of 3 liters per minute each, i.e. a mixture ratio of 50%, and thirdly, O$_2$ alone at a flowrate of 6liters per minute.

The provision for immediate selection of such commonly used flowrates and mixture ratios will enable the apparatus to be more rapidly put into operation when necessary, and will reduce the possibility of operator errors occurring when immediate use of the apparatus is required.

Numeral 70 in the control panels of FIG. 2 and FIG. 5 denotes a digital time display section. This can be driven to provide an elapsed time indication to notify the duration of an operation, or can be equipped with a time alarm function, to sound an alarm warning when a predetermined time has elapsed.

Figures 6, 6A:
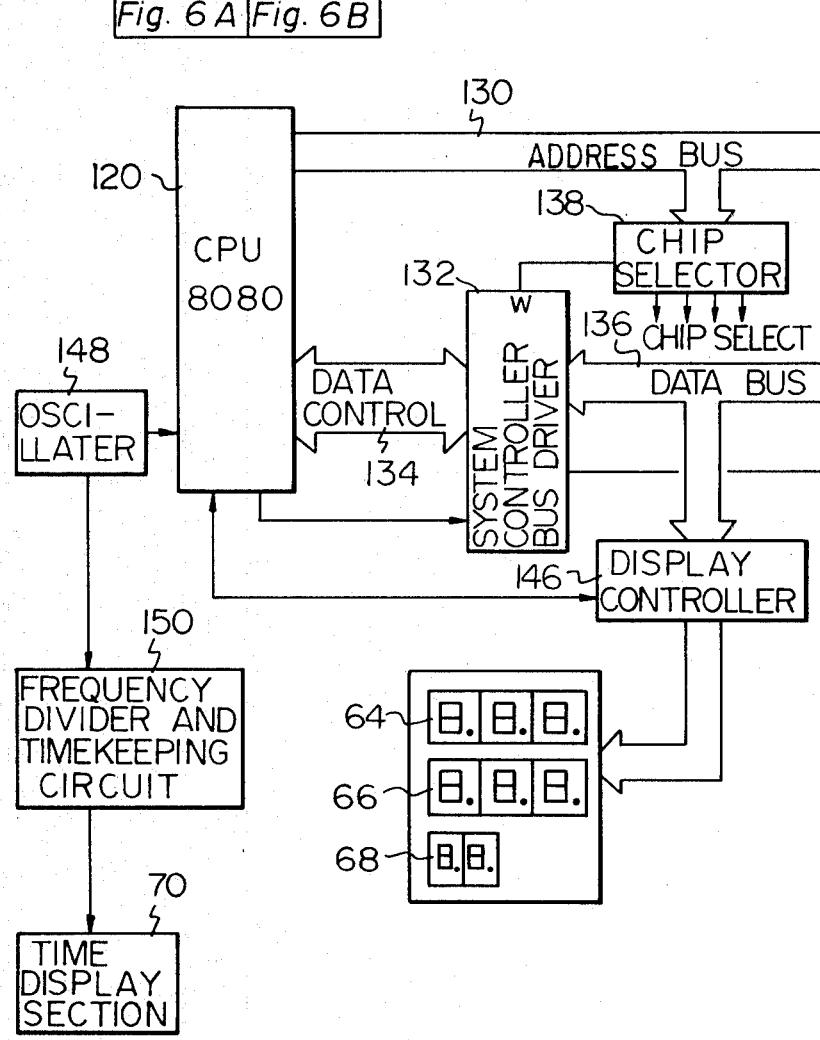
FIG. 6 is a general block diagram to illustrate the flow of data in the electronic control system of an apparatus according to the present invention.
Figure 6B:
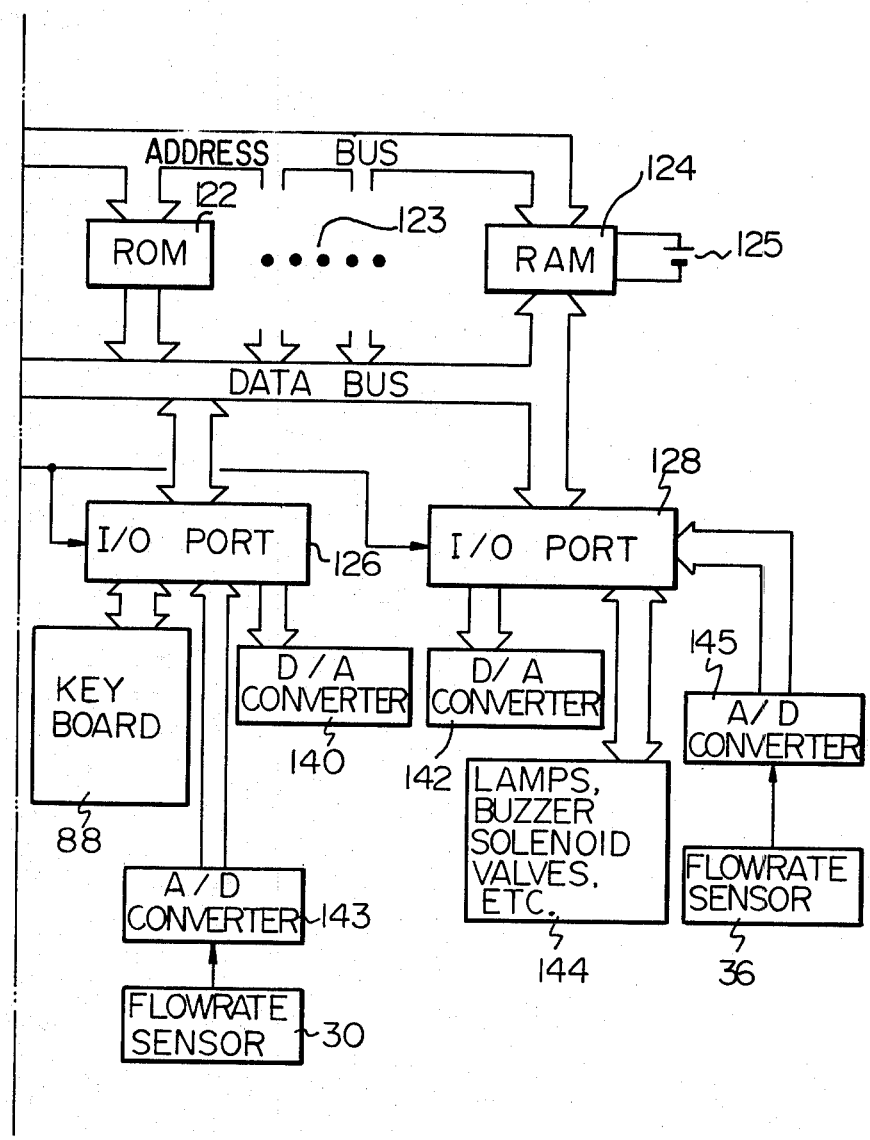

FIG. 6 is a block diagram illustrating the general configuration of an embodiment of electronic control system 40. This control system 40 comprises all of the blocks shown in FIG. 6, with the exception of a keyboard 88 (corresponding to input device 42 of FIG. 1) and a light-emitting diode (LED) display denoted by numerals 64, 66 and 68 (corresponding to display device 44 of FIG. 1). These keyboard and display components have been described above, with relation to the control panel configurations of FIG. 2 and FIG. 5. In addition, numeral 144 denotes various lamps, an alarm buzzer, and solenoid valves 20 and 22, which are actuated by means of signals produced by electronic control system 40.

Control system 40 is based upon a central processing unit (abbreviated hereinafter to CPU) 120. Among the signals which CPU 120 produces are address signals, which are output to an address bus 130. In this embodiment, the various components of control system 40 comprise integrated circuit chips, which include read-only memory chips (usually referred to as ROMs), which may be of programmable type (i.e. PROMs) and also random access memory chips (RAMs). In FIG. 6, a ROM is denoted by numeral 122, while numeral 124 denotes a RAM. Various other memory chips may be provided if necessary, as indicated by numeral 123. ROM 122 is used to store data which will frequently be used during operation of the apparatus. Such data includes for example commonly used flow rate and mixture ratio data, such as that which is selectable by means of keys 117, 118 and 119 in the control panel embodiment of FIG. 5. RAM 124 is used to store data which is only required temporarily, i.e. data which is input by means of keyboard 88 numeric keys to designate the desired flow rate and mixture ratio for a particular surgical operation before that operation is commenced. Normally, data stored in a random access type of integrated circuit memory is volatile, i.e. will be lost in the event of a failure of the power supply to the integrated circuit. For that reason, RAM 124 is powered by a back-up battery 125, in order to be independent of any failure of the apparatus power supply. Thus, if there is a power failure during use of the apparatus, and if that failure is only temporary, it is possible for the flow rate and mixture ratio data stored in RAM 124 to be immediately put into use when electronic control of the anesthetic gas flow is resumed, following recovery from the power failure.

Selection of a particular memory chip for addressing, and of an address in the selected memory chip is performed by means of address selection which are produced by CPU 120. These signals also serve as control signals under some circumstances. Data which is input to and output from ROM 122 and RAM 124 is carried on a data bus 136, under the control of system controller and bus driver section 132. The system controller and bus driver section also serves to control the flow of data which is to be input to the CPU 120 and control signals which are output from the CPU, between CPU 120 and data bus 136. In order to achieve this, the system controller and bus driver section 132 discriminates between control signals from the CPU 120 and data signals, and produces independent control signals in accordance with the results of such discrimination. The latter independent control signals serve to control read and write operations of ROM 122 and RAM 124, and also to control the flow of data into and out of the system, which takes place through input/output ports 126 and 128, and also through a display controller 146. The results of operations by CPU 120 are displayed on display sections 64, 66 and 68 by means of signals transferred through display controller 146.

Numeric data and various input control signals are input to control system 40 from keyboard 88, through input/output port 126. Input data indicating the flow rates of oxygen and N$_2$O gases are applied from flow rate sensors 30 and 36 to analog-to-digital converters (hereinafter abbreviated to A/D converters) 143 and 145 respectively. The digital signals thus produced are input through input/output ports 126 and 128 to data bus 136, and hence to CPU 120. CPU 120 compares the data represented by these signals with the data stored beforehand in memories 122 or 124, and generates output signals in accordance with the degree of difference between the actual flow values measured by flowrate sensors 30 and 36 and the stored data values for the flowrates (determined by the mixture ratio and total flowrate data). These output signals from the CPU 120 are transferred through input/output ports 126 and 128 to digital-to-analog converters (hereinafter abbreviated to D/A converters) 140 and 142, which produce analog output signals to drive throttle valves 26 and 34 respectively. In this way, the flow of O$_2$ and N$_2$O is controlled by throttle valves 26 and 34 in such a way as to eliminate any difference between the actual flowrates of O$_2$ and N$_2$O gases and the flowrate values represented by the previously stored data.

The transfer of data through display controller 146 to display sections 64, 66 and 68 is done by what is called "direct memory access". In this method, the CPU 120 is periodically halted, and the addresses of the memory locations containing the display data are output to the address bus 130. The display data thus output from the memory are then stored in latch circuits and used in driving the display device. In this embodiment, each of display section 64, 66 and 68 is composed of light-emitting diodes (LEDs).

Input of data from the keys of keyboard 88 is accomplished by means of what is called the "software scan" method. In this, one terminal of each key switch of keyboard 88 is connected an input terminal of an input/output port, while the other terminal of that key switch is connected to an output terminal of the input/output port. These terminals of the input/output port are successively and repetitively scanned, e.g. by successively applying a signal to each input terminal. When it is detected that the input/output port input and output terminals coupled to a particular key switch remain at the same potential level during this scanning process, then this indicates that the key concerned has been actuated (i.e. the key switch contacts are closed). In actual practice, the connections to the keyboard switches are arranged in the form of a matrix, in order to reduce the amount of wiring required, but the basic principle of operation is as described above.

Numeral 148 denotes an oscillator which produces a standard frequency timebase signal. This signal serves as a clock pulse signal which times the operation of electronic control system 40, and also is applied to the input of a frequency divider circuit 150, the output of which constitutes a time unit signal from which time information signals are produced to drive time display 70, shown in FIG. 2 and FIG. 5.

Circuit arrangements for generating such time information signals from a timebase signal are well known, and therefore will not be described. Such circuit arrangements include means whereby current time or elapsed time can be computed, and an alarm signal generated after a predetermined time has elapsed, if such a function is required. In addition, timing signals produced by means of oscillator 148 timebase signal are used in measuring the cumulative consumption of $O_2$ and $N_2O$. This is done by measuring the volume of each gas (measured by means of flowrate sensors 30 and 36) which flows during each predetermined time interval (e.g. per minute).

Figure 7B:
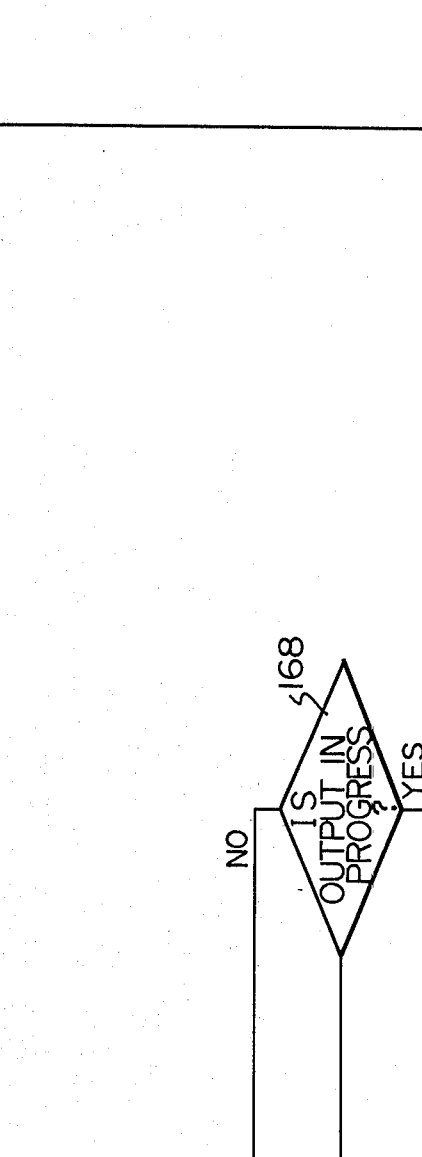
FIG. 7 is a flow chart illustrating the process whereby the electronic control system controls the apparatus according to the present invention.
Figure 7C:
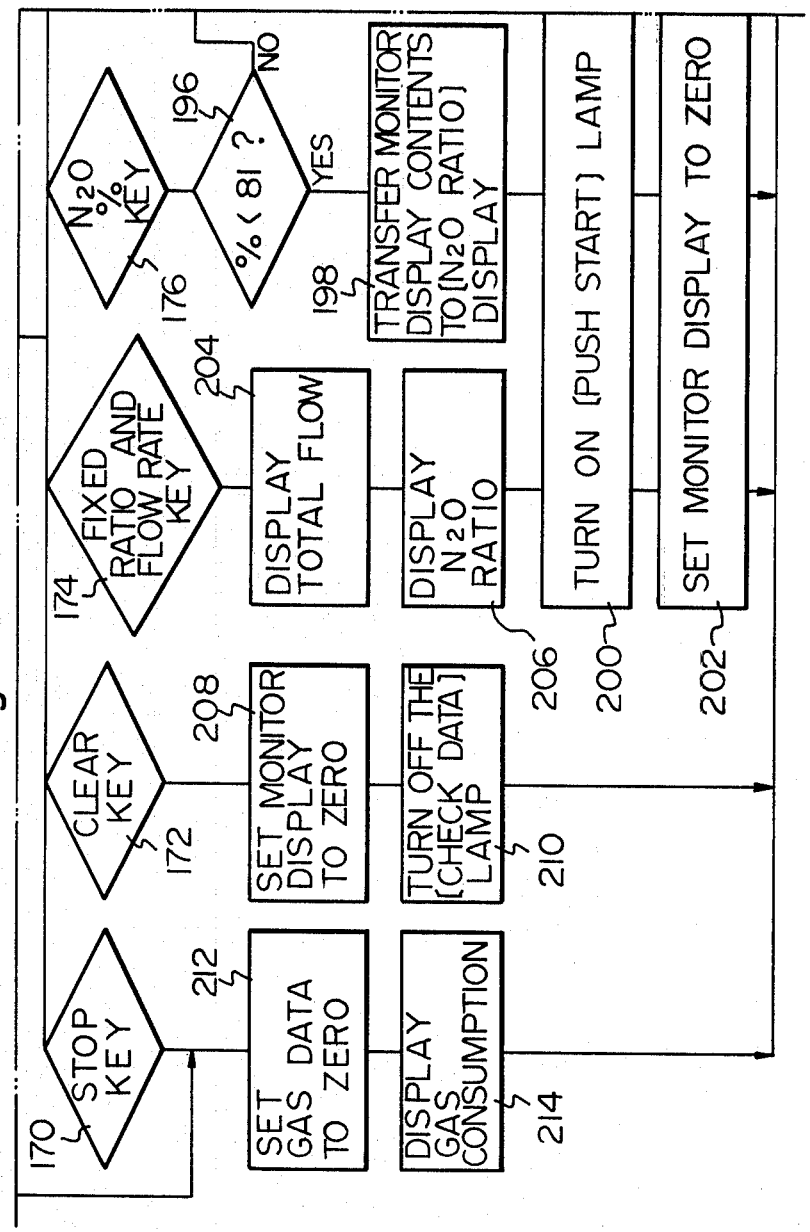
Figure 7D:
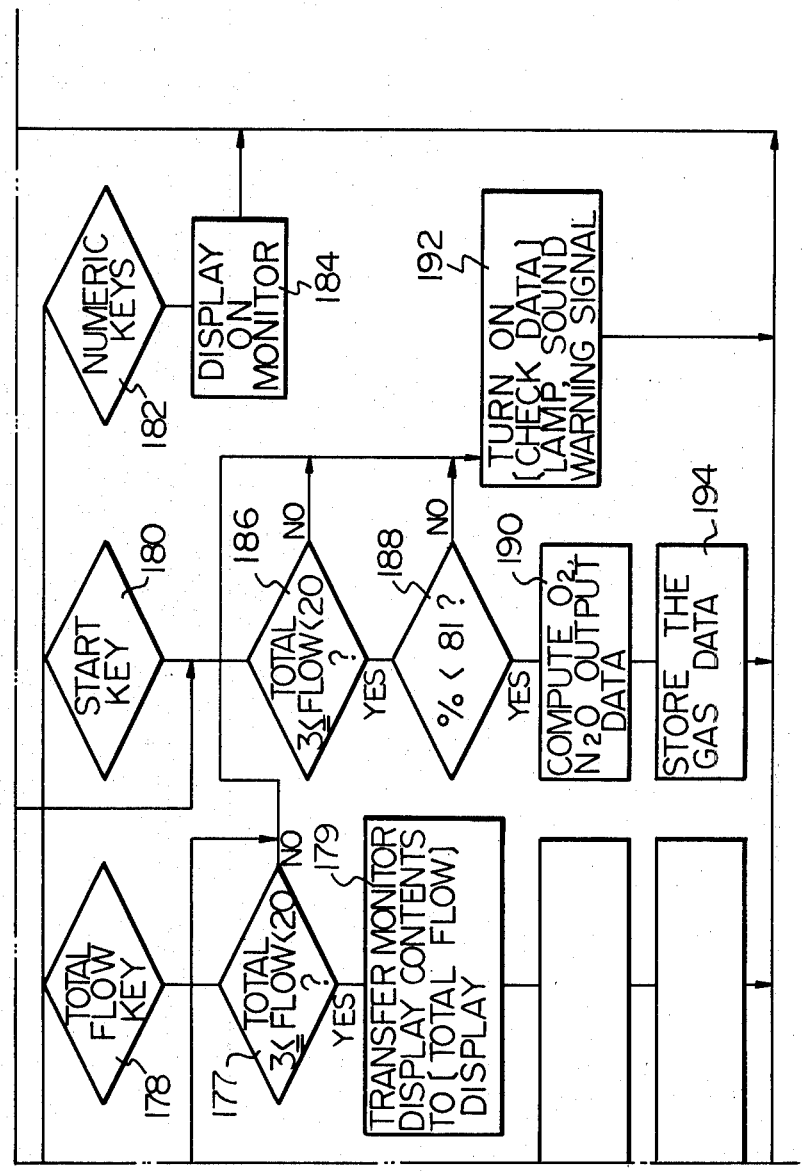

Referring now to FIG. 7, a flow chart is shown therein to describe the operation of the electronic control system 40, from a program aspect. Preparation for entering the program is performed by generation of an initial setting signal, which causes various control signals to be produced for initialization of control system 40 and which sets a "stack" pointer. In the preferred embodiment, this initial setting signal is generated when power is applied to the apparatus, either due to the power switch being closed or due to recovery from a power supply failure taking place. Once this initial setting signal has been generated, as indicated by numeral 156, then a judgement is made as to whether operation of the apparatus is being started as a result of the power supply switch (i.e. switch 104 shown in FIG. 4) being closed, or whether a power supply failure had occurred previously and that recovery from that failure has resulted in power being applied to the apparatus. In the latter case, it will be necessary to retain the previously stored data which specifies the required total flowrate and mixture ratio for the anesthetic gas. This is due to the fact that such recovery from a power supply failure could occur during the progress of a surgical operation, and in such a case it would be desirable to immediately return to electronic control of the gas flow and mixture ratio (by actuating changeover handle 14 in FIG. 1 from the "fixed control" to the "electronic control" position, as described hereinabove). On the other hand, if the generation of the initial reset signal has occurred due to the power switch being closed, then this indicates that a new surgical operation is about to begin. In this case it is necessary to delete the previously input data for gas mixture ratio and flowrate, and to also delete the previously computed data for cumulative gas consumption, since such data are stored in non-volatile memory means, as described hereinabove. Thus, if the judgement is made that power failure recovery has occurred, i.e. a YES decision is made in block 158, then a program sequence is entered in which data specifying total flowrate and mixture ratio for the anesthetic gas are computed based on the stored data, and output to digital/analog converters 140 and 142, to control throttle valves 26 and 34. However, for ease of explanation, the program sequence for normal operation will first be described i.e. when power is applied normally, by the operator actuating the power switch.

When the power is switched on, then an initial reset signal is generated, in step 156. The system then judges that power failure has not occurred beforehand, and that new data will therefore be used to specify the gas flowrate and mixture ratio, so that the previously stored data specifying these must be cleared, together with the previously computed data on total gas consumption. The program therefore proceeds first to step 162, in which the previous cumulative gas consumption data is cleared, and then to step 212, in which the previous stored data specifying the gas mixture ratio and the total gas flowrate (which data we shall abbreviate simply to "gas data" in the following description of the program sequence) are cleared. The program then proceeds to step 214, in which the cumulative gas consumption (at this point it is of course zero) is displayed. The program sequence then goes to step 160, in which the gas data is to be output to the D/A converters, to drive the throttle valves 26 and 34, although at this stage such data has not yet been computed. In step 160, the cumulative gas consumption is computed, and the program then moves to step 166. In this step, a check is made to determine whether any of the keys on keyboard 88 are being actuated. If none of the keys is being actuated at this time, then the program moves to step 168, in which a check is made as to whether gas data is being output (i.e. to the D/A converters to drive throttle valves 26 and 34). Since the requisite data has not yet been input to the control system, a NO judgement is made at this time, so that the program returns to step 166. The program will therefore remain in a closed loop, circulating between steps 166 and 168, until one of the keys on keyboard 88 is actuated. In the flow rate diagram of FIG. 7, it is assumed that fixed, i.e. permanently stored, data specifying mixture ratio and total flowrate are provided, as in the embodiment described above with respect to FIG. 5. This fixed data can be selected by the operator actuating a corresponding key, whereupon the key actuation is detected by the system. A YES judgement is therefore made in step 166, and the program sequence proceeds to step 176, and hence to step 204. Here, the fixed data specifying the total gas flowrate is displayed, and is made available to CPU 120 for gas data computation purposes. The program then proceeds to step 206, in which the fixed data specifying the mixture ratio, i.e. the relative proportion of $N_2O$ to $O_2$, is displayed and is made available to CPU 120. At this point, in step 200, the "PUSH START" display indicator 78 is turned on. When the start key 92 is depressed, the contents of the monitor displays are cleared, in step 202. The program sequence then returns to step 160 and then to step 164 and 166. A judgement is now made in step 166 that a key (i.e. the start key) has been depressed, i.e. a YES decision, so that the program now proceeds through step 180 to step 186. In this step and the succeeding one, the gas data is checked to confirm that it lies within predetermined limits for the total flow (in step 186) and for the mixture ratio (in step 188). If a YES judgement is made in both of these steps, then the program proceeds to step 190. If the gas data is not within the predetermined limits, then the program proceeds to step 192, in which the CHECK DATA indicator is turned on, to notify the operator that there is a discrepancy in the gas data.

In step 190, the central processing unit 120 compares the actual flow of $O_2$ and that of $N_2O$ with the values specified by the stored data, and produces the gas data. The values of the gas data are determined by the differences between the actual gas flow values, as input through A/D converters 143 and 145 from flowrate sensors 30 and 36, and the stored data. The gas data is then stored, in step 194, and the program sequence returns to step 160. The stored gas data is now output to D/A converters 140 and 142, the output signals from which control throttle valves 26 and 34 to provide gas flows as specified by the fixed data for total flowrate and mixture ratio.

After step 164, since no key is being actuated at this time, the program proceeds to step 168. The system now judges that output is in progress, i.e. gas data is being utilized to control the flow of $O_2$ and $N_2O$. A YES decision is therefore made in step 168, and the sequence proceeds to step 186 once more.

Thereafter, until the operation is terminated or a power failure occurs, the program enters a loop, proceeding through steps 188, 190, 194, 160, 164, 166, 168, and 186. In each pass through this loop, the gas data is recalculated, and a check is made that the values obtained are within the predetermined limits. This is extremely important, since in the event of an error being set into the gas data due to some reason such as pickup of electrical interference, such a temporary error will have no effect upon the operation, if it is due to a momentary cause. If on the other hand the cause of the error is of a long-term nature, a warning will be delivered to the operator, in the form of an audible alarm signal and the CHECK DATA indicator being turned on. If the gas data were only computed once and the resultant values stored and used continuously, any error entering the gas data could have a very dangerous effect.

The program sequence will now be described for the case in which data are entered by means of the numeric keys of keyboard 88, to specify the mixture ratio and total flowrate. After power is switched on, thereby performing initial setting of the control system as described above, the program sequence proceeds as described previously until the loop is entered in which the program circulates between steps 166 and 168. At this time, the keyboard keys are being scanned to detect actuation of any of them. If the operator now actuates numeric keys 88 so as to input data, then a YES decision is made in step 166, and the program proceeds through step 182 to 184, in which the data which has been input is displayed on monitor display 68. The program then returns through steps 160 and 164 to the key scanning loop of steps 166 and 168. If the data which has been input is intended to specify the total flowrate, the operator then actuates key 191. The data is then checked in step 177 to determine if it is within the predetermined limits. If not, an audible alarm is sounded and the CHECK DATA warning indicator goes on. If the data is approved, it is transferred to be displayed on display section 64 of control panel 67, and the "TOTAL FLOW" display indicator goes on. The operator should then depress the START key 92 (the "PUSH START" indicator is turned on in step 200) and the monitor display is then cleared. The program sequence then proceeds through steps 160, 164, 180, 186, 188, 190, 194, 160, 164 and back into the loop of steps 166 and 168. The same procedure is then repeated in order to input the mixture ratio data from the numeric keys. When this has been done, the program sequence proceeds again to step 190. At this time, the CPU 120 computes the required values for oxygen and $N_2O$ flow, based on the input data, and stores this as the gas data. Thereafter, the sequence of operations is identical to that described above, for the case of using fixed data to specify mixture ratio and total flowrate.

In order to terminate operation of the system, the STOP key 93 is actuated. As a result, the gas data is set to zero, and the cumulative consumptions of $O_2$ and $N_2O$ are displayed, in steps 212 and 214.

If the CHECK DATA indicator is turned on, the operator must first determine the reason for this and correct it, and then depress the CLEAR key 87. The contents of the monitor display are then cleared to zero, and the CHECK DATA lamp is turned off, in steps 208 and 210.

Measurement of the gas consumption during step 164 is performed on a time measurement basis. The flowrates of $O_2$ and $N_2O$ are converted into a volume of gas per predetermined unit of time (e.g. per minute), and the time units are added up while the apparatus is supplying gas, to thereby compute the cumulative gas consumption data.

Figure 8:
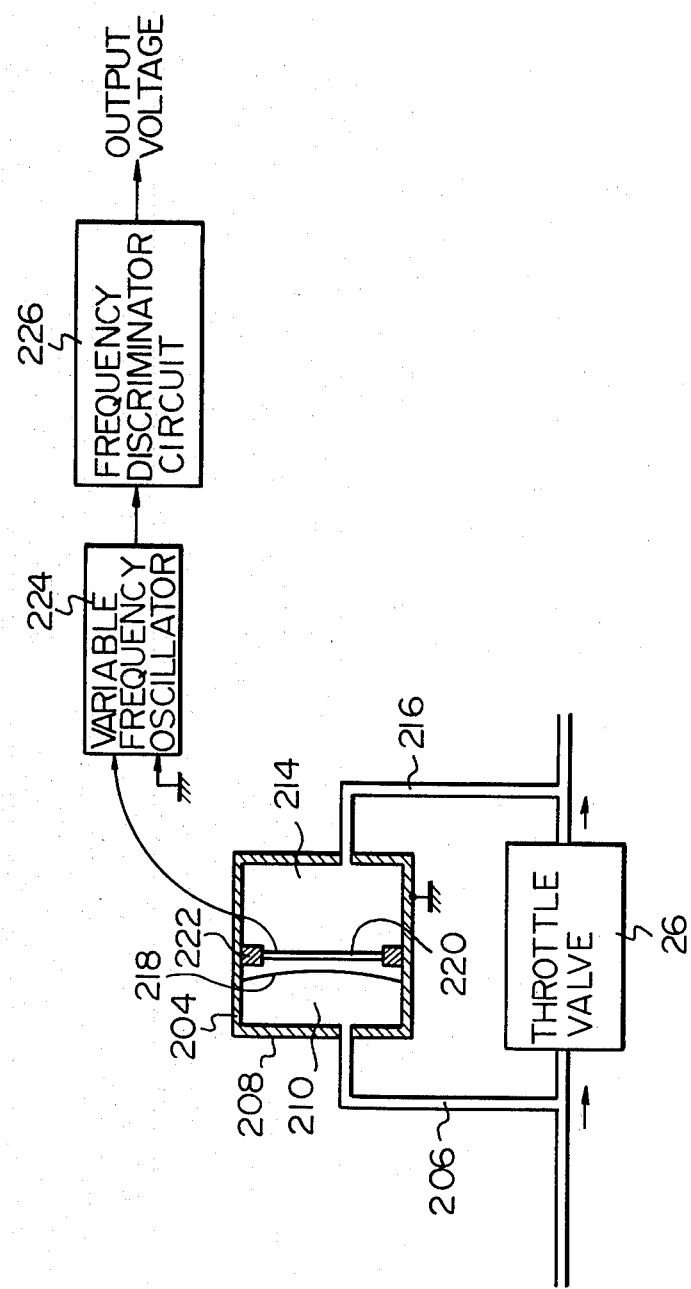
FIG. 8 is a diagram illustrating an embodiment of a flowrate sensor.

An embodiment of flowrate sensor 30, for measurement of the flow of $O_2$, will now be described. Flowrate sensor 36 is of identical configuration. Referring to FIG. 8, a diagram illustrating the general configuration of such a sensor is shown. Its principal components are an enclosed gastight chamber 204, a variable frequency oscillator circuit 224, and a frequency discriminator circuit 226. Chamber 204 comprises an outer casing 208, and contains a flexible metallic diaphragm 218 which divides chamber 204 into two separate compartments, 210 and 214. A fixed electrode 220 is attached inside chamber 204 adjacent to flexible diaphragm 218, by insulated support means 222. An opening in casing 208 serves to couple oxygen gas through a pipe 206 to the interior of left-hand chamber 210, from the inlet side of throttle valve 26. A similar pipe 216 couples the output side of throttle valve 26 to the interior of right-hand chamber 214. Fixed electrode 220 permits unobstructed application of pressure from pipe 216 to flexible diaphragm 218. Fixed electrode 220 is electrically connected to the input of a variable frequency oscillator circuit 224, which produces an output signal to be applied to the input of a frequency discriminator circuit 226.

The operation of this flowrate sensor is as follows. When throttle valve 26 is being controlled by an electrical signal to pass a flow of oxygen, a pressure differential is developed across the input and output sides of the throttle valve. This pressure differential is transmitted through pipes 206 and 216 to the interiors of chambers 210 and 214, thereby deflecting flexible diaphragm 218 towards fixed electrode 220. The capacitance between fixed electrode 220 and flexible diaphragm 218 is thereby increased, and this capacitance change results in a change of the oscillation frequency of variable frequency oscillator circuit 224. This change in frequency is detected by frequency discriminator circuit 226, which produces an output voltage whose amplitude varies in accordance with the frequency of the output from variable frequency oscillator 224. This output signal is then converted to a digital signal by means of an analog-to-digital converter, and utilized in computing gas data as described hereinabove.

From the preceding description, it will be apparent that the objectives set forth for the present invention are effectively attained. Since various changes and modifications to the above construction may be made without departing from the spirit and scope of the present invention, it is intended that all matter contained in the above description or shown in the accompanying drawings shall be interpreted as illustrative, and not in a limiting sense. The appended claims are intended to cover all of the generic and specific features of the invention described herein.

What is claimed is:

1. An apparatus for supplying a predetermined rate of flow of an anasthetic gas comprising a mixture of a first gas and a second gas, said first and second gases being provided from a first gas source and a second gas source, said apparatus comprising:

a first electrically controlled throttle valve coupled to receive said first gas from said first gas source, for producing a controlled flow thereof;

a second electrically controlled throttle valve coupled to receive said second gas from said second gas source, for producing a controlled flow thereof;

first flowrate sensing means for measuring the rate of flow of said first gas when output from said first electrically controlled throttle valve and for producing electrical signals of digital form indicative of the magnitude of said rate of flow;

second flowrate sensing means for measuring the rate of flow of said second gas when output from said second electrically controlled throttle valve and for producing electrical signals of digital form indicative of the magnitude of said rate of flow of the second gas;

data input means for generation of digital data to specify a predetermined total rate of flow of said anasthetic gas and to specify a predetermined mixture ratio of said first and second gases;

an electronic control system coupled to receive said digital electrical signals from said first flowrate sensing means and from said second flowrate sensing means and to receive said digital data from said data input means, and comprising memory circuit means for storing said digital data from said data input means and digital data processing circuit means for comparing said predetermined total rate of flow of said anasthetic gas and said predetermined mixture ratio of said first and second gases as represented by said stored digital data with an actual total rate of flow of said anasthetic gas and an actual mixture ratio of said first and second gases as represented by said digital electrical signals from said first and second flowrate sensing means and for producing control signals on the basis of said comparison, said control signals being applied to said first and second electrically controlled throttle valves for thereby bringing said actual total rate of flow of anasthetic gas and actual mixture ratio of said first and second gases into coincidence with said predetermined total rate of flow of said anasthetic gas and said predetermined mixture ratio of said first and second gases respectively;

electro-optical display means for displaying said predetermined total rate of flow of said anasthetic gas and said predetermined mixture ratio of said first and second gases stored in said memory circuit means; and means for mixing said first and second gases after measurement of the rates of flow thereof by said first and second flowrate sensing means, for thereby providing said anasthetic gas further comprising first and second fixed throttle valves having the outputs thereof coupled to said means for combining the first and second gases; and manually actuated gas switching means for selectively supplying either (1) said first gas from said first gas source to said first electrically controlled throttle valve and said second gas from said second gas source to said second electrically controlled throttle valve, or (2) said first gas from said first gas source to said first fixed throttle valve and said second gas from said second gas source to said second fixed throttle valve, and further comprising pressure controlled gas switch means located downstream of said second fixed throttle valve and responsive to pressure from said first gas source to allow flow of said second gas past said gas switch means only when the pressure of said first gas source is above a predetermined minimum pressure.

2. An apparatus for supplying an anasthetic gas according to claim 1, in which each of said first and second flowrate sensing means comprises a flowrate sensor responsive to a gas flow for producing electrical signals to indicate the magnitude thereof and an analog-to-digital converter circuit for converting said electrical signals into digital electrical signals.

3. An apparatus for supplying an anasthetic gas according to claim 1, wherein said memory circuit means includes non-volatile memory circuit means for storage of said input data, whereby said data is retained in storage in said non-volatile memory circuit means in the event of a cessation of electrical power supply to operate said apparatus.

4. An apparatus for supplying an anasthetic gas according to claim 1, in which said data input means comprises a keyboard including a plurality of keys and a plurality of switches actuated thereby.

5. An apparatus for supplying an anasthetic gas according to claim 1, and further comprising a source of a standard frequency timebase signal, and in which said electronic control system is further operative to compute a volume of each of said first and second gases consumed by said apparatus from said first and second gas sources during each of successive time intervals defined by sad timebase signal and to cumulatively add said computed volumes for thereby computing cumulative consumptions of said first and second gases by said apparatus.

6. An apparatus for supplying an anasthetic gas according to claim 1, and further comprising battery-operated means coupled to said apparatus for detecting failure of electrical power supplied to said apparatus and for generating an audible alarm signal in response to such detection.

7. An apparatus for supplying an anasthetic gas according to claim 1, and further comprising a first solenoid valve coupled to receive said first gas from said first gas source and a second solenoid valve coupled to receive said second gas from said second gas source, each of said first and second solenoid valves being responsive to control signals produced by said electronic control system for selectively establishing an open state in which a supply of gas is enabled or a closed state in which a supply of gas is cut off.

8. An apparatus for supplying an anasthetic gas according to claim 1, in which said display means further comprises warning indication means, and in which gas data representing a difference between said predetermined total rate of flow of said anasthetic gas and said actual total rate of flow of said anasthetic gas and representing a difference between said predetermined mixture ratio of said first and second gases and said actual mixture ratio of said first and second gases is generated by said electronic control system, and further wherein said electronic control system acts to detect when the magnitude of each of said differences exceeds a predetermined limit value and activates said warning indication means to produce a perceptible warning signal when said limit value is exceeded.

* * * * *